US00PP25542P3

(12) United States Plant Patent
Schoone

(10) Patent No.: US PP25,542 P3
(45) Date of Patent: May 12, 2015

(54) ***PHALAENOPSIS* ORCHID PLANT NAMED 'MOONDUST'**

(50) Latin Name: *Phalaenopsis hybrida*
Varietal Denomination: Moondust

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 230 days.

(21) Appl. No.: 13/573,581

(22) Filed: Sep. 26, 2012

(65) Prior Publication Data

US 2013/0086720 P1 Apr. 4, 2013

Related U.S. Application Data

(60) Provisional application No. 61/540,883, filed on Sep. 29, 2011.

(30) Foreign Application Priority Data

Sep. 30, 2011 (NL) ..... PBR OPS0837

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Moondust' particularly characterized by flowers which are light yellow with red/purple spots and stripes: the labellum is purple with some yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Moondust'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Moondust'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Moondust' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Moondust' originated from a cross made by the inventor in 1999 in Strengweg, Heemskerk, The Netherlands. The female or seed parent is the *Phalaenopsis* cultivar designated 'Fortune Buddha', unpatented. The male or pollen parent is the *Phalaenopsis* cultivar designated 'Taipei Gold', unpatented. The new *Phalaenopsis* 'Moondust' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture (mericloning) was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Moondust', which in combination distinguish this *Phalaenopsis* as a new and distinct cultivar:

1. flowers which are light yellow with red/purple spots and stripes; the labellum is purple with some yellow;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Moondust', the female parent 'Fortune Buddha' has yellow flowers with many red/purple spots and stripes, the male parent 'Taipei Gold' has yellow/green colored flowers with a white/pink mark in the center, whereas the flowers of 'Moondust' are light yellow with at the center some red/purple spots and stripes.

Presently, the most similar cultivars to the claimed variety are the parental cultivars, to which a comparison has been provided above.

BRIEF DESCRIPTION OF THE PHOTOGRAPHS

The accompanying photographs illustrate the overall appearance of the new *Phalaenopsis* 'Moondust' showing the colors as true as is reasonably possible with colored reproductions of this type. Colors in the photographs may differ slightly from the color values cited in the detailed botanical description, which accurately describe the color of 'Moondust'.

DETAILED BOTANICAL DESCRIPTION

Figure 1:
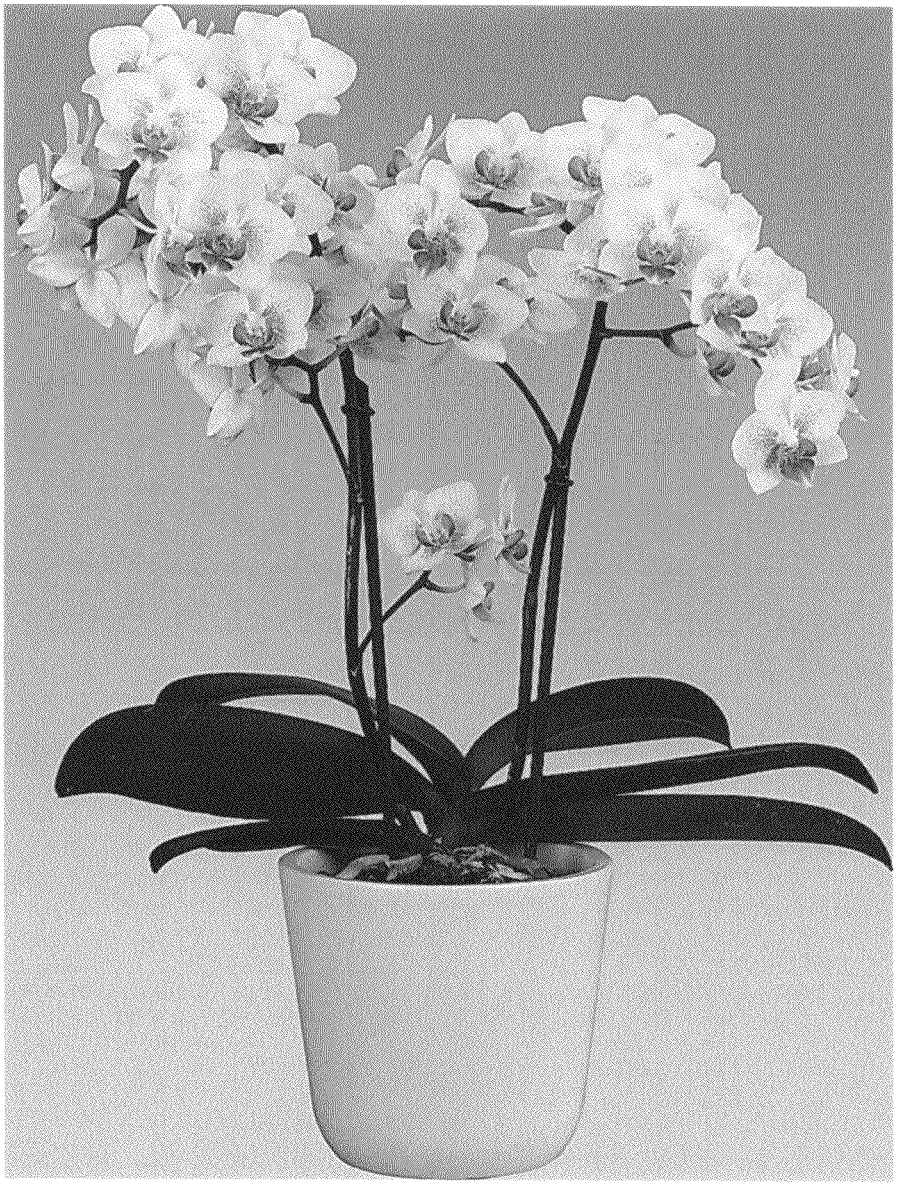
FIG. 1 shows a side view perspective of a typical flowering plant of 'Moondust' in a 12 cm pot, at 16 months of age.

The new *Phalaenopsis* cultivar 'Moondust' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Moondust' as grown in a greenhouse in Strengweg, Heemskerk, The Netherlands, under conditions which closely approximate those generally used in commercial practice. Initially, the ideal temperature to grow plants of 'Moondust' is 27° C. during the day and at night. Then, during the flowering phase of 'Moondust', the ideal growing temperature is 20-22° C. during the day and 18° C. at night. Light levels for growing 'Moondust' are a minimum of 5,000 lux and a maximum of 10,000 lux. A balanced fertilizer with level of 200 ppm N, 87 ppm P, 168 ppm K is applied. Duration of growth of 'Moondust' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Moondust' plants described is 12 months after potting.

Classification:

*Botanical.*—*Phalaenopsis hybrida.*

Parentage:

*Female or seed parent.*—*Phalaenopsis* cultivar designated 'Fortune Buddha', unpatented.

*Male or pollen parent.*—*Phalaenopsis* cultivar designated 'Taipei Gold', unpatented.

Propagation:

*Type.*—Tissue culture (mericloning).

*Rooting habit and description.*—Fleshy; approximately 4 mm-8 mm wide and green/yellow in color (RHS 146C); freely branching. It takes 12 weeks for plants growing in tissue culture to initiate roots.

Plant:

*Size at maturity.*—Height (from bottom of pot to top of highest flower): about 40 to 45 cm. Spread: about 35 to 43 cm.

*Growth habit.*—Small; green leaves (RHS 139A) and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1 to 2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, tip is blunt and asymmetric.

*Texture* (*both surfaces*).—Smooth and leathery.

*Pubescence.*—None.

*Base.*—Acute.

*Margin.*—Entire.

*Mature leaf length.*—About 16 to 21 cm.

*Mature leaf width.*—About 9 to 11 cm.

*Mature leaf thickness.*—About 2 mm.

*Mature leaf color.*—Upper surface: RHS 139A; under surface: RHS 137B.

*Venation.*—Pattern: parallel. Color of midvein: upper surface: RHs 147A; under surface: RHS 139B.

Raceme:

*Quantity per plant.*—About 1 to 2.

*Number of flowers per raceme.*—About 10 to 15.

*Length.*—About 36 to 40 cm.

*Diameter.*—About 4 to 6 mm.

*Strength.*—Strong.

*Aspect.*—Upright.

*Texture.*—Glabrous and smooth.

*Color.*—Green (RHS 137B).

*Internode.*—Length: about 23 to 30 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 to 20 mm. Diameter (at midpoint): about 10 to 15 mm. Shape: egg-shaped. Color: yellow/green (RHS 144B). Orientation: same as flowers (forward facing).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1 to 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—Darker/younger flowers no fragrance; lighter/older flowers fragrance.

Figure 2:
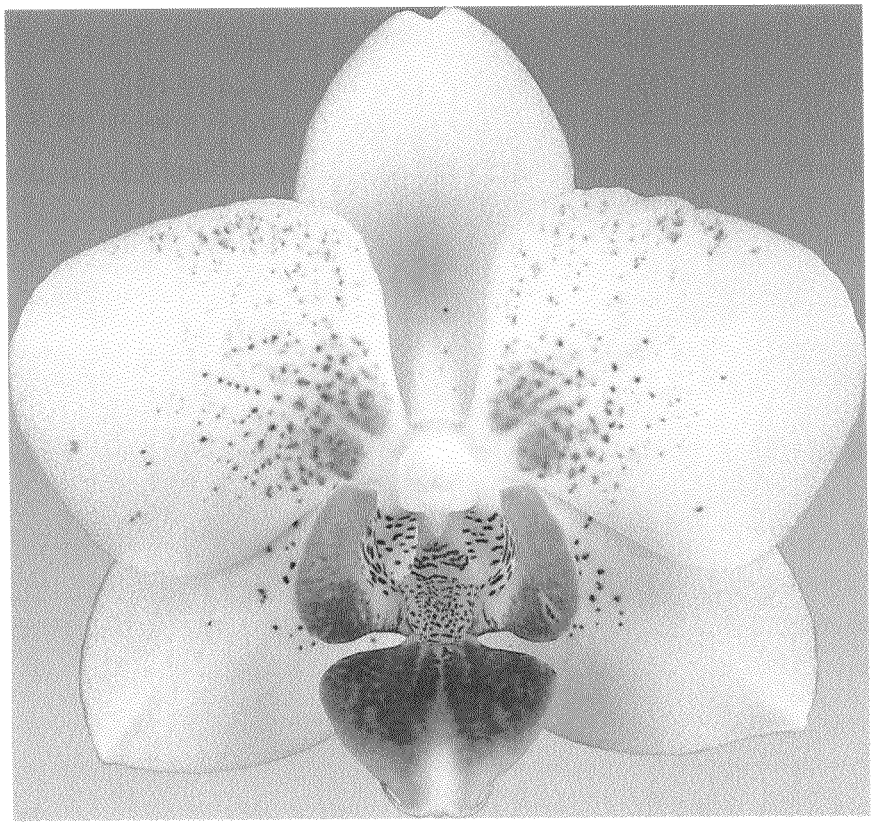
FIG. 2 shows a close-up view of the typical flower of 'Moondust'.
Figure 3:
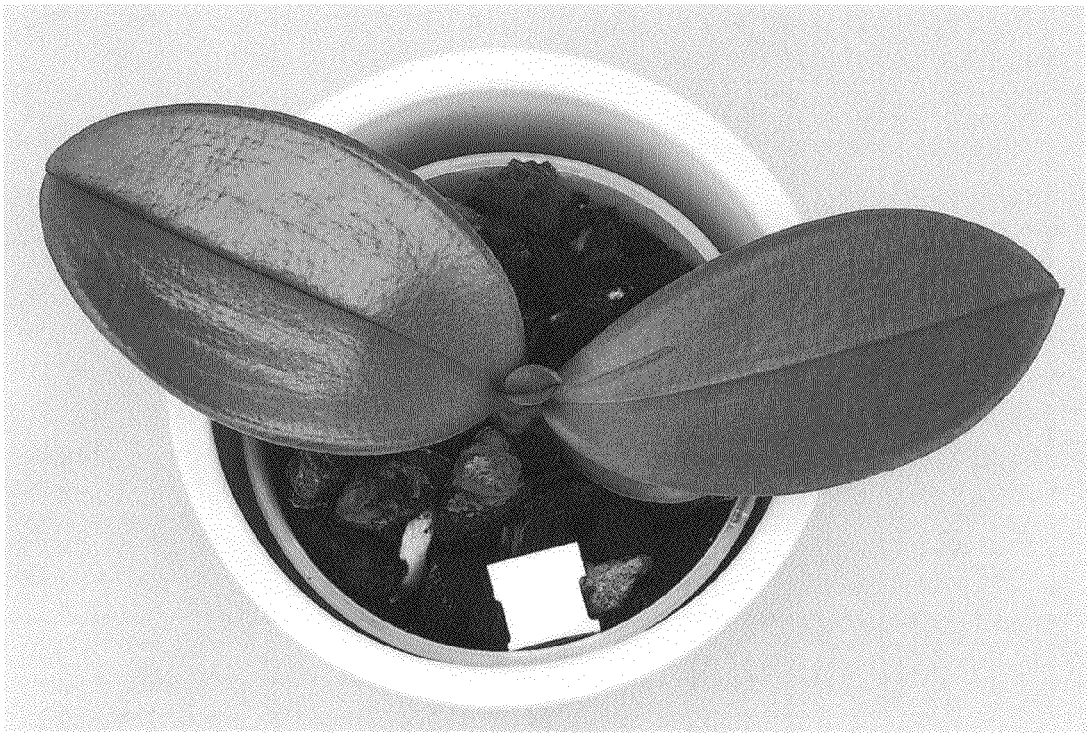
FIG. 3 shows a close-up view of the typical leaves of 'Moondust'

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 45 to 55 mm. Diameter: about 50 to 55 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: little bit triangular/broadly ovate and weakly cupped. Apex: oval. Margin: entire and weakly undulate. Base: broadly ovate. Length: about 22 to 27 mm. Width: about 22 to 28 mm. Texture: Upper surface: smooth and satiny. Under surface: smooth and satiny. Color (when fully opened): Main color is yellow (RHS 4D) (The younger/newer flowers are green/yellow (RHS 1 C), mainly at the base some red/purple spots and stripes (RHS N74B). Under surface: older flower is white (RHS 155A), younger flower is green/yellow (RHS 1C). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire and weakly undulate. Length: about 19 mm. Width (not flattened): about 15 mm. Depth of tube (made from lateral lobes): about 8 mm. Texture: Upper & under surface: smooth and satiny. Color (when fully opened): Main color of the Mid lobe and the lateral lobes is purple (RHS N78B); mid lobe has red/purple spots (RHS 60B). At the base yellow (RHS 7A). Also a yellow line in the center and yellow thin edges (RHS 7A). Lateral lobes: lower edge is red/purple (RHS 60B) and the rest is yellow (RHS 6C) with red/purple spots and stripes (RHS 59A). Cirrhi: two small points. Color: yellow (RHS 5B). Pestle (Callosities): Length: about 4 mm. Width (not flattened): about 5 mm. Height: about 5 mm. Color: yellow (RHS 7A) with red/purple spots and stripes (RHS 59A).

*Sepals*.—Arrangement: Outer whorl comprises 3 sepals. Overall shape: elliptical and weakly cupped; v-shaped hole on top of dorsal sepals. Length: about 25 to 33 mm. Width: about 20 to 22 mm. Texture: Upper & under surface: smooth and satiny. Color (when fully opened): young flower upper surface: green/yellow (RHS 1 C) with red/purple spots & stripes (lateral sepal RHS 60A, dorsal sepal RHS N74B). Under surface is green/yellow (RHS 1 C). Older flower upper surface: yellow (RHS 4D) with red/purple spots & stripes (lateral sepal RHS 60A, dorsal sepal RHS N74B). Under surface is yellow (RHS 4D).

*Pedicel*.—Length: about 23 to 30 mm. Diameter: about 3 mm. Texture: glabrous and smooth.

*Color*.—Base is green (RHS 136B), middle is yellow/green (RHs 147C) and close to flower is (RHS 75B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 8 mm. Diameter: about 5 mm. Color: white (RHS NN155C).

*Pollinia*.—Quantity: Two. Size: about 1 mm. Color: orange (RHS 24A).

*Ovary*.—Length: about 4 mm. Diameter: about 5 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Moondust', as illustrated and described herein.

* * * * *